United States Patent
Laskavy et al.

(10) Patent No.: US 8,673,575 B2
(45) Date of Patent: Mar. 18, 2014

(54) METHOD FOR CARRYING OUT A QUALITATIVE PRELIMINARY INSTANT DIAGNOSIS OF ONCOLOGIC DISEASES

(76) Inventors: Vladislav Nikolaevich Laskavy, Saratov (RU); Sergei Ivanovich Ivanenko, Moscow (RU)

( * ) Notice: Subject to any disclaimer, the term of this patent is extended or adjusted under 35 U.S.C. 154(b) by 455 days.

(21) Appl. No.: 12/737,306

(22) PCT Filed: Feb. 27, 2009

(86) PCT No.: PCT/RU2009/000094
§ 371 (c)(1),
(2), (4) Date: Dec. 28, 2010

(87) PCT Pub. No.: WO2010/008315
PCT Pub. Date: Jan. 21, 2010

(65) Prior Publication Data
US 2011/0097703 A1    Apr. 28, 2011

(30) Foreign Application Priority Data
Jul. 17, 2008    (RU) ................. 2008129535

(51) Int. Cl.
*G01N 33/53*    (2006.01)
*G01N 33/555*    (2006.01)

(52) U.S. Cl.
USPC .................. 435/7.1; 436/64; 436/520

(58) Field of Classification Search
None
See application file for complete search history.

(56) References Cited

FOREIGN PATENT DOCUMENTS

| | | |
|---|---|---|
| RU | 2140641 | 10/1999 |
| RU | 2219549 | 12/2003 |
| RU | 2309405 | 10/2007 |

OTHER PUBLICATIONS

Freshney, 'Culture of Animal Cells', 3rd ed., 1994, p. 72.*
Brock, 'Biology of Microorganisms', 3rd ed., 1979, p. 776.*
English Abstract of RU2111492 downloaded from Espacenet on Dec. 12, 2013.*
The machine translation of RU2111492 downloaded from Espacenet on Dec. 12, 2013.*
SPEV cell line information downloaded from RCCC on Dec. 12, 2013.*
Selected Coagulation Disorders Associated with Cancer. Sabah Sallah, In Vivo, 1998, vol. 12, 671-674.

\* cited by examiner

*Primary Examiner* — Karen Canella
(74) *Attorney, Agent, or Firm* — Aleksandr Smushkovich

(57) ABSTRACT

The invention relates to medicine, in particular to a method for carrying out a preliminary instant diagnosis of oncologic diseases. The method involves sampling a patient's blood, mixing the sample with a reagent and recording reaction results. A supernatant liquid, which is produced by cultivating the finite cell line of a porcine embryo kidney culture in anaerobic conditions, is used as a reagent. The presence of oncologic disease is determined according to a positive reaction of erythrocytes and a negative or positive reaction of a citrated blood with the reagent. The inventive method makes it possible to make a preliminary conclusion about the presence of oncologic disease within a short time.

2 Claims, No Drawings

METHOD FOR CARRYING OUT A QUALITATIVE PRELIMINARY INSTANT DIAGNOSIS OF ONCOLOGIC DISEASES

CROSS-REFERENCE TO RELATED APPLICATIONS

This application is a U.S. national stage application of a PCT application PCT/RU2009/000094 filed on 27 Feb. 2009, published as WO/2010/008315, whose disclosure is incorporated herein in its entirety by reference, which PCT application claims priority of a Russian Federation application RU2008129535 filed on 17 Jul. 2008.

FIELD OF THE INVENTION

The invention is related to medicine, specifically, to oncology and can be used for a quick and precise blood diagnostics to make a preliminary conclusion on whether there is malignancy or not.

BACKGROUND OF THE INVENTION

Early diagnostics and detection of malignancies is an important medical problem. Various methods are used for cancer diagnostics, such as X-ray, endoscopic, ultrasonographic, morphologic, as well as measurement of the DNA concentration in blood or serum of malignant patients. However, these methods are inefficient for the detection of malignant transformation and at early disease stages.

A method of early diagnostics of cancer is known, which is based on the measurement of blood levels of intracellular nucleic acids bound to cellular surface of hemocytes (Russian Federation Patent No. 2251696, published on May 10, 2005). The zero value of this parameter is attributed to malignancy.

A main drawback of the aforementioned method is in that it is intricate.

Another method of diagnostics of malignancies is known which is based on the measurements of blood biochemical values such as levels of vitamins A and E and iron-dependent organ-specific antibody-like proteins possessing false SOD-activities (Russian Federation Patent No. 2021612, published on Oct. 15, 1994).

However, this method is time-consuming, highly expensive, and requires special equipment to be used.

Most closely related to the claimed method is a method for qualitative early express diagnostics of malignancy (see Russian Federation Patent No. 2309405, published on Oct. 27, 2007) that involves the following steps: collection of a blood sample; addition of a reagent containing a polar solvent and a non-polar water-soluble alcohol; filtration of the mixture; separation of the upper colored water-alcoholic solution (a supernatant); and evaluation of the reaction outcome by comparing the color of the filtrate with colored controls prepared in a similar way from the blood of a knowingly healthy subject and malignant patients at different stages of the disease.

However, the above-described method does consider an immune reaction of the body because it is based on a non-specific reaction. Furthermore, it requires a considerable amount of blood (25 mL) to be collected, which can make the patients feel worse.

The goal of the present invention is to develop a simple, efficient and precise method of early express diagnostics of malignancies which would consider the body's immune reaction to the presence of malignant cells and their activities products and also be of low cost.

To achieve the goal, the method of precise early express diagnostics of malignancies, which involves collecting a blood sample, mixing it with a reagent and evaluating the reaction outcome, is modified, in accordance with the present invention, by additionally preparing 0.12-0.5% suspensions of citrated blood and washed erythrocytes, both from the same patient; using, as a reagent, a supernatant liquid obtained as a result of growing a porcine embryo kidney finite cell culture in anaerobic conditions; separately mixing suspensions of citrated blood and washed erythrocytes with the reagent and incubating at 4-8° C. for 12-15 h; and separately evaluating the outcomes of reactions of citrated blood and washed erythrocytes. Based on this method, the patient is concluded malignant if the reaction of erythrocytes is positive while the reaction of citrated blood is either negative or positive, as well as if the reaction of erythrocytes is negative and the reaction of citrated blood is positive.

To the authors' knowledge, no data are available in the related art patents and scientific technical literature on an efficient, simple, and quick method of qualitative preliminary express diagnostics of malignancies using a reagent in the form of a supernatant liquid obtained as a result of growing a porcine embryo kidney finite cell culture (SPEV-line) in anaerobic conditions.

The method is based on—evaluating the outcomes of reactions of both citrated blood and washed erythrocytes obtained from the same patient with the reagent in the form of a supernatant liquid obtained as a result of growing a porcine embryo kidney finite cell culture (SPEV-line), and—the phenomenon of immune response regulation.

Previous studies demonstrated the presence of C and D onco-RNA-viruses in the latent form in the SPEV cell culture that was grown in anaerobic conditions (see Laskavyi, V. N., Dyakonova, L. P., and Melnikova, G. V. Culture and accumulation of oncogenic viruses in anaerobic conditions. Veterinamyi Vrach, 2004, no. 2, pp 32-38). In the studies, the cells were grown in the Eagle 199 medium for 3 to 5 days at a medium-to-air phase ratio of 1:5.

The authors have used a supernatant liquid obtained as a result of growing SPEV cells containing C and D viruses in latent form for malignancies diagnostics. The SPEV cells culture is commonly used as a substrate to isolate and accumulate various viral agents.

The phenomenon of immune response regulation registered as Discovery No. 385 dated Jun. 28, 2006, consists in that a system of self-regulation of an organism's immunity involves, apart from T- and B-lymphocytes, red blood cells. Being a part of the hematopoietic system, the immunocompetent cells are capable of interacting with other components of hematopoiesis (in particular, with erythroids) and experience regulatory effects caused by the latters.

The mechanism of reaction of citrated blood and washed erythrocytes is based on a natural interaction between erythrocytes having immunoglobulins or immunoglobulin complexes on their surfaces with a reagent, being a supernatant liquid obtained as a result of growing SPEV cells in the anaerobic conditions (for 3 to 5 days at a medium-to-air phase ratio of 1:5) which contains C and D onco-RNA-viruses in the latent form.

Thus, the immunoglobulins absorbed on the surface of erythrocytes can interact with activities products of the malignant cells. It is this interaction that appears as reactions of citrated blood and erythrocytes with the reagent.

When malignant cells are in excess, the reaction with citrated blood may not occur. However, washed erythrocytes which are free of activities products of malignant cells can enter into a reaction with the reagent, giving a positive reaction.

There is known a method of diagnostics of infectious diseases in animals that is based on evaluation of the outcomes of reaction of citrated blood and agglutination of erythrocytes, both from the same animal and in the presence of the same antigen (Russian Federation Patent No. 2111492, published on May 20, 1998). However, the mentioned method is designed to diagnose infectious diseases in animals, in particular, viral infections such as swine fever and transmissible gastroenteritis. As a reagent, the method uses viral antigens in the form of supernatant liquid obtained as a result of growing the corresponding virus in the SPEV cell culture as substrate.

No data are available on the use of a supernatant liquid obtained as a result of growing SPEV cells alone (without any virus) in anaerobic conditions for the diagnostics of malignancies.

Based on the aforesaid, it can be concluded that the claimed invention meets the "inventive level" criteria.

DETAIL DESCRIPTION OF PREFERRED EMBODIMENTS OF THE INVENTION

While the invention may be susceptible to embodiment in different forms, there are described in detail herein, specific embodiments of the present invention, with the understanding that the present disclosure is to be considered an exemplification of the principles of the invention, and is not intended to limit the invention to that as described herein.

The inventive method is carried out as follows.

1-2 mL of blood is collected from a patient's ulnar vein and transferred to tubes with a stabilizer (either sodium citrate or heparin).

Part of the citrated blood is used to prepare 0.12-0.5% suspensions in a saline solution. For this, a volume of from 83 mL (0.12% suspension) to 20 mL (0.5% suspension) of the saline solution is added to the 0.1-mL sample of blood of the patient.

The remaining citrated blood is diluted with a saline solution at 1:10, and erythrocytes are washed off by triply centrifugating each sample for 10 minutes at 3000 rpm. To prepare 0.12-0.5% suspensions, a volume of from 83 mL to 20 mL of saline solution is added to each 0.1-mL sample of the precipitated erythrocytes.

A supernatant liquid, obtained as a result of growing SPEV cells in anaerobic conditions and used as the reagent, is prepared in advance. For this purpose, SPEV cells in culture are seeded on the Eagle 199 medium and incubated at 37° C. during from 3 to 5 days at a medium-to-air phase ratio of 1:5. After cellular breakdown, the matter is frozen and thawed, then centrifuged for 30 min at 3000 rpm, and the supernatant liquid is taken.

The reactions are run on special plates with indentation cups. Two sets of the indentation cups are used simultaneously, one for citrated blood, and the other for washed erythrocytes.

Saline solution in the amount of 0.2 mL is added to each indentation cup in one row of the cups in both sets.

All the indentation cups are filled with 0.5 mL of 0.12-0.5% suspensions of either citrated blood (in the first set) or erythrocytes (in the second set).

The indentation cups containing the saline solution and suspensions are considered control cups.

The reagent in the amount of 0.2-0.3 mL is added to each indentation cup, except for the control cups.

The sets are both incubated at 4-8° C. for 12-15 h, and then outcomes of the reactions are evaluated.

The formation of residue shaped like an umbrella with irregular boundaries all over the surface of the indentation cup is interpreted as a 'positive' reaction. The formation of residue shaped like a button or point at the bottom of the indentation cup is interpreted as a 'negative' reaction.

The reaction in the control indentation cups must be always negative. Concentrations of citrated blood and washed erythrocytes (0.12-0.5%), amount of the reagent to be added (0.1-0.3 mL) and the temperature of incubation (4-8° C.) of mixtures for 12 to 15 h were determined experimentally.

It was found that at the suspension concentrations bellow 0.12% and the reagent amounts below 0.2 mL, neither citrated blood nor erythrocytes were actually resulted in a reaction, while at the suspension concentrations above 0.5% and the reagent amounts above 0.3 mL the reactions were flat (weak) and their outcomes were difficult to interpret.

The temperature of incubation of citrated blood and washed erythrocytes with the reagent was also determined experimentally. Tree temperature modes were tested: 22° C. (room temperature), 37° C., and 4-8° C. It was found that at 22° C. and 37° C. the reactions were flat and their outcomes were difficult to interpret.

A combination of the positive reaction of erythrocytes and the negative reaction of citrated blood is indicative of an excess of malignant cells activities products and a significant activation of immune response.

A combination of the positive reaction of erythrocytes and the positive reaction of citrated blood is indicative of a minor amount of malignant cells activities products and activation of immune response.

A combination of the negative reaction of erythrocytes and the positive reaction of citrated blood is indicative of a significant but inefficient activation of immune response to malignant cells activities products.

Example 1

Male patient A, 56 years old. 2 mL of blood were collected from the patient's ulnar vein and transferred to a tube with heparin. A part of citrated blood was used to prepare a 0.25% suspension in saline solution. For this, 40 mL of saline solution were added to each 0.1-mL sample of the blood.

The remaining citrated was diluted with saline solution at 1:10, and erythrocytes were washed off by triply centrifugating each sample for 10 minutes at 3000 rpm. Then, to prepare a 0.25% suspension, 40 mL of saline solution were added to each 0.1-mL sample of the resude.

The reagent was prepared in advance by collecting the supernatant liquid obtained as a result of growing SPEV cells in anaerobic conditions.

Two sets of indentation cups were used to simultaneously run the reactions with citrated blood and washed erythrocytes. Saline solution in the amount of 0.2 mL was added to each indentation cup in one row of the indentation cups in both sets.

Into all of the indentation cups 0.5 mL of a 0.25% suspension of either citrated blood (first set) or erythrocytes (second set) were added.

The indentation cups containing saline solution and suspensions were considered controls.

The reagent in the amount of 0.2 mL was added to each indentation cup, except for the control indentation cups.

Both the sets were incubated at 4-8° C. for 12-15 h, and then outcomes of both the reactions were evaluated.

The reaction with citrated blood was found negative, and the reaction with washed erythrocytes was found positive. Subsequently, patient A underwent the examination by ultrasound and cytological methods and was more precisely diagnosed with melanoma of the skin of the anterior peritoneal wall.

Example 2

Female patient B, 58 years old. Hemanalysis was performed as in Example 1. The reaction with citrated blood was found positive and with washed erythrocytes negative. Subsequently, the patient was more precisely diagnosed with left breast cancer.

Example 3

Male patient C, 74 years old. Hemanalysis was performed as in Example 1. Both the reactions were found positive. Subsequently, the patient was more precisely diagnosed with colonic cancer.

In total, 42 patients were examined by the claimed method. Forty of them (95%) were diagnosed with malignancies which were subsequently confirmed by commonly accepted diagnostic methods. In one patient with a positive reaction, a malignancy was diagnosed a year later.

In the control group (n=12), the diagnosis was confirmed in no case. Thus, the claimed method allows for an early, quick, and precise detection of malignancy. The method can be useful in conducting the screening of the population and will help to offer patients medical advice and effective treatment at an early stage of the disease.

The invention claimed is:

1. A method for carrying out a qualitative preliminary instant diagnosis of oncologic diseases, said method comprising the steps of:
   collecting a predetermined amount of blood sample from a patient and preparing therefrom:
      a first suspension of citrated blood having a concentration of 0.12%-0.5%, and
      a second suspension of washed erythrocytes having a concentration of 0.12-0.5%;
   supplying a reagent in the form of supernatant liquid, obtained as a result of growing SPEV-line cells in anaerobic conditions;
   mixing separately said reagent with said first suspension of citrated blood thereby obtaining a first mixture, and with said second suspension of washed erythrocytes thereby obtaining a second mixture;
   incubating said first mixture and said second mixture at 4-8° C. for 12-15 hours;
   evaluating the outcomes for said first and second mixtures by determining individual reactions for citrated blood and washed erythrocytes with said reagent; and
   judging the presence of cancer by a positive reaction of erythrocytes and a negative or a positive reaction of citrate blood, as well as by a negative reaction of erythrocytes and a positive reaction of citrated blood.

2. The method according to claim 1, wherein said predetermined amount of blood sample constitutes from 1 to 2 mL of blood, and is collected from the patient's ulnar vein.

* * * * *